(12) United States Patent
Bissinger et al.

(10) Patent No.: US 7,807,730 B2
(45) Date of Patent: Oct. 5, 2010

(54) COMPOSITION CONTAINING UNSATURATED SILICONE COMPOUNDS, DENTAL MATERIALS CONTAINING THEM AND USE THEREOF

(75) Inventors: Peter Bissinger, Diessen (DE); Joachim W. Zech, Kaufering (DE)

(73) Assignee: 3M Espe AG, Seefeld (DE)

( * ) Notice: Subject to any disclaimer, the term of this patent is extended or adjusted under 35 U.S.C. 154(b) by 846 days.

(21) Appl. No.: 11/247,040

(22) Filed: Oct. 11, 2005

(65) Prior Publication Data

US 2006/0111464 A1    May 25, 2006

(30) Foreign Application Priority Data

Oct. 12, 2004    (EP) .................................. 04024243

(51) Int. Cl.
*A61C 5/08* (2006.01)
*C08G 77/12* (2006.01)
*C08G 77/20* (2006.01)
*C08L 83/05* (2006.01)
*C08L 83/07* (2006.01)

(52) U.S. Cl. .......................... 523/113; 528/10; 528/15; 524/588; 433/228.1

(58) Field of Classification Search .................. 528/10, 528/15; 524/588; 523/113; 433/228.1
See application file for complete search history.

(56) References Cited

U.S. PATENT DOCUMENTS

| | | | |
|---|---|---|---|
| 3,715,334 | A | 2/1973 | Karstedt |
| 3,775,352 | A | 11/1973 | Leonard |
| 3,814,730 | A | 6/1974 | Karstedt |
| 3,933,880 | A | 1/1976 | Bergstrom et al. |
| 4,877,854 | A | 10/1989 | Hattori et al. |
| 5,086,148 | A | 2/1992 | Jochum et al. |
| 5,137,448 | A | 8/1992 | Dougherty et al. |
| 5,264,606 | A | 11/1993 | Moloy et al. |
| 5,312,860 | A | 5/1994 | Mize et al. |
| 5,849,812 | A | 12/1998 | Zech et al. |
| 6,252,101 | B1 | 6/2001 | Herzig et al. |
| 6,313,190 | B1 | 11/2001 | Bublewitz et al. |
| 6,335,413 | B1 | 1/2002 | Zech et al. |
| 6,512,037 | B1 | 1/2003 | Ahn et al. |
| 2004/0044164 | A1 | 3/2004 | Engelbrecht |
| 2004/0110863 | A1 | 6/2004 | Zech et al. |
| 2005/0159522 | A1 | 7/2005 | Bublewitz et al. |

FOREIGN PATENT DOCUMENTS

| | | |
|---|---|---|
| DE | 3741575 A1 | 6/1988 |
| DE | 19719438 A1 | 11/1997 |
| DE | 10261917 A1 | 7/2004 |
| EP | 0503975 A2 | 9/1992 |
| EP | 0940405 B1 | 9/1999 |
| EP | 1475069 A1 | 11/2004 |
| EP | 1652889 A1 | 5/2006 |
| WO | WO 96/32088 A | 10/1996 |
| WO | WO 97/40102 A | 10/1997 |
| WO | WO 02/11680 | 2/2002 |
| WO | WO 02/078647 A | 10/2002 |

OTHER PUBLICATIONS

Encyclopedia of Polymer Science and Engineering, $2^{nd}$ edition, vol. 15, pp. 204-308.
J. Burghardt, Chemie und Technologie der Polysiloxane in "Silikone, Chemie und Technologie", Vulkan Verlag, Essen, 1989, pp. 23-37.
Iwahara, et al., "Synthesis of New Organic Crosslinking Reagents Containing SiH bonds and Curing System Thereof" Polymer Journal, vol. 25, No. 4, pp. 379-389 (1993).
W. Noll, "Chemie und Technologie der Silikone", Verlag Chemie Weinheim, $2^{nd}$ edition, 1968, pp. 162-206.
Wiley, John; Stuart, Barbara, "Polymer Analysis", ISBN 0471899267, (Bb), pp. 108-112.
DIN 53505.
DIN 53453—superseded by DIN EN ISO 179.
DIN 51048-1—superseded by DIN EN 993-7.
DIN 51048-2—superseded by DIN EN 993-6.
DIN 53455—superseded by DIN EN ISO 527-2 and 527-1.
DIN 53454—superseded by DIN EN ISO 604.
DIN 53018-1.

*Primary Examiner*—Tae H Yoon
(74) *Attorney, Agent, or Firm*—Ann Mueting

(57) ABSTRACT

The invention relates to a curable composition comprising addition curable silicone component (A) having a linear siloxane backbone at least one unsaturated, non-activated side group pendant from the Si atom or atoms in the backbone, component (A) having an equivalent weight in the range of about 68 to about 1000, crosslinker component (B) comprising at least 2 SiH groups, catalyst component (C) being able to catalyse the reaction between component (A) and component (B), filler component (D), wherein the equivalent weight is defined as (molecular weight of the molecule)/(number of unsaturations in the molecule).

20 Claims, No Drawings

COMPOSITION CONTAINING UNSATURATED SILICONE COMPOUNDS, DENTAL MATERIALS CONTAINING THEM AND USE THEREOF

This application claims priority from European Application Serial No. 04024243.0, filed Oct. 12, 2004.

The invention relates to a curable composition comprising an addition curable component having a relatively high number of unsaturated side groups as well as to a method of producing this component. The component and the composition comprising this component are especially useful for the production of dental materials.

Hydrosilation as a mechanism of curing is used, e.g., in curable compositions resulting in elastomeric three-dimensional shapes or in coatings. The materials in question usually show little mechanical resistance and are either rubber-like or brittle. Formulations cured by hydrosilation are not likely to lead to three-dimensional shapes with mechanical resistance adequate for dental restoration, cements or provisional crowns and bridge materials.

In U.S. Pat. No. 5,849,812 A1, an addition crosslinkable, polyether impression material is described that comprises an organopolysiloxane with at least two alkenyl groups.

U.S. Pat. No. 6,335,413 B1 describes curable materials containing organo hydrogen polysiloxane dendrimers with at least three SiH groups in the molecule, a catalyst, fillers and at least one silane dendrimer with terminal alkenyl groups. The patent indicates that the materials obtained after curing have an increased hardness and a viscosity suitable for processing in the dental field. A Shore hardness D of the materials after 24 hrs of 41 is reported. The patent indicates that the materials can be used for bite registration, temporary and permanent filling materials, crown and bridge materials as well as cements and varnishes.

U.S. Pat. No. 6,313,190 B1 describes addition cross-linkable, two-component, silicone materials based on polysiloxane, wherein after cross-linking via a hydrosilation reaction, the silicone materials have a Shore hardness D of greater than 35 and a modulus of elasticity of greater than 20 MPa. The patent indicates that these materials can be used for bite impressions.

All the aforementioned materials have disadvantages. For example, the materials lack the desired combination of properties desired for dental materials such as low viscosity before curing, and adequate hardness after curing. Therefore, there is a need for alternative compositions, especially for use in the dental field.

The invention relates to a curable composition comprising:
   addition curable silicone component (A) having a linear siloxane backbone, at least one unsaturated, non-activated side group pendant from the Si atom or atoms in the backbone, component (A) having an equivalent weight in the range of about 68 to about 1000;
   crosslinker component (B) comprising at least 2 SiH groups;
   catalyst component (C) able to catalyse a reaction between component (A) and component (B); and
   filler component (D), wherein the equivalent weight is defined as (molecular weight of the molecule/(number of unsaturations in the molecule), total number of carbon-carbon double bonds in component (A) is at least 3, and wherein the unsaturated, non-activated side group does not comprise a —O—Si—CH=CH$_2$ moiety.

Some of the embodiments of the invention have improved properties, e.g., high hardness after curing and some embodiments also have relatively low viscosity before curing.

The terms "comprise" and "contain" within the meaning of the invention introduce a non exhaustive list of features. Likewise, the word "one" or "a" is to be understood in the sense of "at least one".

The term "addition curable silicone component" refers to polymers comprising alternating silicon and oxygen atoms (i.e., a polysiloxane-type chemical structure) and having sufficient pendant functional groups to undergo a setting reaction, preferably resulting in a completely cured material in the presence of a crosslinker compound as hereinafter defined and a catalyst material.

The term "crosslinker" refers to polymers that react with the functional group or groups on other polymer chains to lengthen them and connect them, e.g., to form a crosslinked network characteristic like that of a cured silicone elastomer. In contrast to a thermoplastic polymer, (i.e., a polymer that softens and flows upon heating) a crosslinked polymer, after crosslinking, is usually incapable of further flow. Crosslinked polymers differ in some important respects from linear and branched polymers. For example they swell in good solvents to form a gel but do not dissolve to form a solution. At elevated temperature, cross-linked polymers behave like soft but elastic solids rather than viscous liquids.

The term "hydrosilation" means the addition of an organosilicon hydride compound to a compound containing an aliphatic multiple bond (e.g., an olefinic or acetylenic unsaturation), preferably a vinyl group, —CH=CH$_2$ or allyl group.

The term "unsaturated non activated side groups" is defined as a group comprising one or more double carbon-carbon bonds with no electron withdrawing groups, like C=O moieties, adjacent to the unsaturation. Accordingly, this term does not comprise acrylate or methacrylate groups or styrene groups. Vinyl groups directly attached to a silicon atom (e.g. —O—Si—CH=CH$_2$ moieties, sometimes referred to as e.g. vinyl functional siloxanes) are not comprised by the term "unsaturated non activated side groups", either.

The curable composition preferably satisfies at least one, preferably two or more, and sometimes all of the following characteristics after curing:
   Shore hardness D of the cured composition, measured according to DIN 53505, above about 35, preferably above about 45, more preferably at least 55, and even more preferably above about 60. Values up to about 95, up to about 90 or up to about 80 can be reached.
   E-modulus of the cured composition above about 1000 MPa, preferably above about 1200 MPa, and more preferably above about 2000 MPa.
   Impact strength of the cured composition measured according to DIN 53453 above about 1, preferably above about 2 kJ/m$^2$.
   Flexural strength, measured according to DIN 51048, above about 60, and preferably above about 70 MPa.
   Compressive strength, measured according to ISO 7489, above about 100, and preferably above about 110 MPa.
   Representative viscosities for component (A) can be in a range of about 0.01 Pa*s to about 50 Pa*s, or in a range of about 0.1 Pa*s to about 20 Pa*s, or in a range of about 1 Pa*s to about 10 Pa*s, at 23° C.
   Representative values for the molecular weight (Mw) of component (A) can be in a range of about 500 gmole$^{-1}$ to about 100000 gmole$^{-1}$, or in a range of about 1000 gmole$^{-1}$ to about 20000 gmole$^{-1}$ or in a range of about 1500 gmole$^{-1}$ to about 10000 gmole$^{-1}$. The molecular weight can be determined with GPC.

Representative equivalent weights of component (A) can be in a range of about 68 to about 1000, or can be in the range of about 80 to about 500 or in the range of about 90 to about 400, wherein the term equivalent weight is defined as follows:

"equivalent weight" (EW)=(molecular weight)/(number of unsaturations in the molecule)

For example:

| Tetraallylsilane: | Molecular weight: | 192 g/mole |
|---|---|---|
| | Number of unsaturations: | 4 |
| | (EW) = (192 g/mole)/4 = | 48 g/mole |

For molecules having a low molecular weight, the number of unsaturations can be counted (cf. Example 4 given below). For molecules having a higher molecular weight the equivalent weight (EW) can be determined by the titration method described below:

| Device: | 682 Titroprocessor (Metrohm, Switzerland) |
|---|---|
| Chemicals: | 0.1 N Sodium arsenite solution (NaAsO$_2$) |
| | Br$_2$/CH$_2$Cl$_2$ (about 3.2 ml Br$_2$ are disolved in CH$_2$Cl$_2$ p.a.) |
| | Methanol p.a. |
| Electrode: | 6.0431.100 Platinum Titrode (Metrohm, Switzerland) |

The sample to be determined is weighed into a 100 ml Erlenmeyer flask with ground neck (exactness 0.1 mg) and dissolved in 10.0 ml of Br$_2$/CH$_2$Cl$_2$ reagent. After a reaction time of about 2 hours at room temperature, 50 ml of methanol p.a. are added and the sample is titrated with 0.1 N sodium arsenite solution. Together with that two blank values are determined. The average value of these blank values is considered in the calculation.

Calculation:

EW=((weight of sample [mg])*2)/((blank value [ml])−(volume of titration of sample [ml])*(factor of NaAsO$_2$ solution [mole/l]))

The value reported below is the average of three determined values.

The equivalent weight reflects the "density" of unsaturations in the respective molecule. The lower the value of EW, the more unsaturations are present in the molecule. The unsaturated groups present in component (A) take part in the crosslinking reaction with crosslinker component (B). A highly crosslinked polymer usually shows a high hardness after curing.

Component (A) comprises at least 2 and may comprise up to about 50 unsaturated organic side groups attached to Si atoms of the linear siloxane backbone. Each side group can have 1, 2, 3 or more unsaturated moieties. The position of the unsaturation in the side group is preferably terminal for the double carbon-carbon bond. Usually the unsaturations are identical in view of their chemical nature, e.g. only vinyl or only allyl. The total number of carbon-carbon double bonds in component (A) is at least 3, 4, 5, 6, 7, 8 or 10.

Useful compositions can be prepared using component (A) in an amount of about 1 to about 95 wt.-%. Another useful range is from about 5 to about 75 wt.-%. A further useful range is from about 10 to about 60 wt.-%.

Crosslinker component (B) of the curable composition is a SiH-containing component having a SiH functionality greater 1, preferably 2, 3, 4, 5, 6 or more. Component (B) can react with component (A) in the presence of catalyst (C) via hydrosilation reaction. Component (B) can be present in the claimed composition in an amount of about 1 to about 80 wt.-%. Another useful range is from about 5 to about 50 wt.-%. A further useful range is from about 10 to about 40 wt.-%. Component (B) may have a viscosity of greater than about 50 mPa*s, and sometimes greater than about 100 mPa*s.

The molecular weight (Mw) of component (B) can be greater than about 400 g/mole or greater than about 600 g/mole. The molecular weight (Mw) of component (B) does usually not exceed about 10000 g/mole. Thus, the molecular weight (Mw) of component (B) can be within the range of about 400 to about 10000 g/mole. The molecular weight can be determined with GPC.

Suitable compounds for component (B) include siloxane-substituted hydrocarbons or polyethers having at least two SiH groups per molecule, for example like those described in U.S. Pat. No. 5,849,812 (corresponding to DE 19 719 438 A1), the description of which regarding definition, synthesis and preferred embodiments should be considered as part of the invention.

Suitable compounds for components (B) are also described in U.S. Pat. No. 5,086,148 the disclosure of which is incorporated by reference, too, and can be represented by formula (I):

wherein:
A is a straight-chain or branched 2- to 6-valent hydrocarbon radical with 6 to 30 carbon atoms, containing at least one aromatically unsaturated or cycloaliphatic ring, B is a straight-chain or branched, saturated hydrocarbon radical with 2 to 6 carbon atoms, m=2 to 6;

n=0 to 25;

C' represents the radical

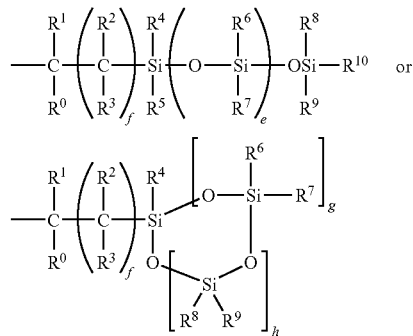

wherein:

$R^0$ to $R^3$ are same or different, and are each H, methyl or ethyl;

e=0 to 8; f=1 to 2; g=0 to 8; h=0 to 4;

$R^4$ to $R^{10}$, are same or different, and are each H, methyl or ethyl, with the proviso that at least 1 and at the most 5 of $R^4$ to $R^{10}$ are H, wherein g and h cannot simultaneously be 0.

In formula (I), radical A can be selected from the group consisting of bivalent 1,4-phenylene, 2,7-naphthylene-, 4,4'-isopropylidenediphenylene-, 4,4'-biphenylylene-, phthaloyl-, terephthaloyl- or tricycle-[5.2.1.02.6]-decan-3,8-dimethyl radicals.

Radical B can be an ethylene or propylene radical, m is preferably from 2 to 4, n is preferably from 0 to 10, and more particularly from 0 to 3. In the radical C', the radicals $R^0$ to $R^3$ are preferably H or methyl, H in particular being preferred, and the radicals are the same, f is preferably 2, $R^4$ and $R^5$ are preferably methyl, $R^6$ is preferably H, $R^7$ and $R^9$ are preferably methyl, $R^8$ and $R^{10}$ are preferably H, e is preferably 0 to 5, and more particularly, 1 to 3, g is preferably 1 to 4 and h is preferably 1 to 2. Radical C' of the following formulas are particularly preferred:

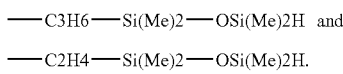

and:

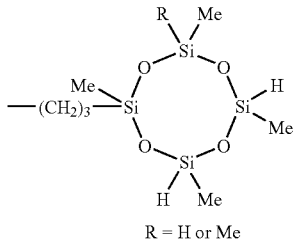

R = H or Me

Especially preferred are compounds according to the formulas below:

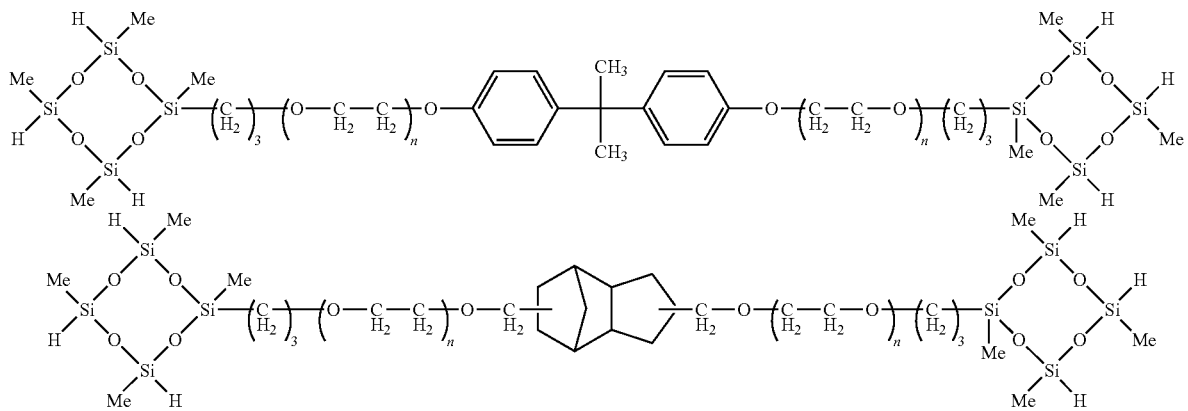

wherein n=0, 1, 2 or 3.

The siloxane-substituted aromatic or cycloaliphatic compounds can be produced according to methods known to the skilled person or as disclosed in U.S. Pat. No. 4,877,854 the disclosure of which is herein incorporated by reference (corresponding to DE 37 41 575 A1). They can be produced by reacting a di- or poly-allyl or -vinyl aromatic compound with a polyorganosiloxane, which contains at least two SiH groups, using a platinum catalyst in a mole ratio of at least two SiH groups to one allyl- or vinyl-group. Suitable starting substances, are for example, the diallylether of bisphenol A, of ethoxylated bisphenol A and of bishydroxymethyl-tricyclo-[5.2.1.0.sup.2,6]-decan as well as phthalic and terephthalic acid diallyl ester. The catalyst used should be removed to produce storage-stable pastes. This can suitably be achieved by the adsorption of the catalyst with silica gel, diatomaceous earth or the like.

Suitable hydrosilation catalyst components (C) which can be used in the invention include those compounds which promote or facilitate the addition reaction between the ethylenically unsaturated groups and the silicon-bonded hydrogen groups of components (A) and (B), respectively.

The catalyst can contain Pt and can be a Karsted catalyst. The catalyst can be prepared from hexachloroplatinum acid by reduction with tetramethyldivinyldisiloxane. Such compounds are known to the skilled person. Any other platinum compounds which can catalyze or accelerate addition cross-linking of silanes with ethylenically unsaturated double bonds are also suitable. Platinum-siloxane complexes as described, e.g., in U.S. Pat. No. 3,715,334, U.S. Pat. No. 3,775,352 and U.S. Pat. No. 3,814,730 are suitable. The disclosure of these patents with regard to platinum complexes and their preparation is explicitly mentioned and expressly regarded as part of the disclosure of the invention.

The amount of the platinum complex catalyst should be sufficient to provide the desired degree of crosslinking of the organopolysiloxane compound within a reasonable time. Due to the wide range of acceptable molecular weights for the addition-curable compound, it is presently believed that this amount is best described in terms of the ratio of Pt atoms to functional groups in the composition. Thus, catalyst component (C) can be used e.g. in an amount of about 0.00005 to about 0.05 wt.-%. Another useful range is form about 0.0002 to about 0.04 wt.-%, each calculated as elemental platinum and related to the overall weight of the composition.

Examples of suitable catalysts include platinum or platinum compound catalysts exemplified by chloroplatinic acid, a complex of chloroplatinic acid and an alcohol, a complex of platinum and an olefin, a complex of platinum and a ketone, a complex of platinum and a vinylsiloxane, colloidal platinum, a complex of colloidal platinum and a vinylsiloxane etc., palladium, a mixture of palladium black and triphenylphosphine, etc., or rhodium or rhodium compound catalysts. Preferred is a complex of Pt with 1,1,3,3-tetramethyl divinyldisiloxane.

The composition of the invention also includes filler component (D), preferably a mixture of fillers. A wide variety of inorganic, especially hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4 to 6 µm); amorphous silicone dioxides, such as a diatomaceous earth (4 to 7 µm); and silanated fumed silica, such as Cab-o-Sil TS-530 (160-240 m$^2$/g), manufactured by Cabot Corporation. Varying the sizes and surface areas of the foregoing materials enables one to control the viscosity and thixotropicity of the resulting compositions. Some or all of the foregoing hydrophobic fillers may be surface treated with one or more silanating agents, as known to those of ordinary skill in the art. Such silanating may be accomplished, e.g., using known halogenated silanes or silazides.

Filler component (D) can be present in an amount of from about 4 to about 90 wt.-%, or about 20 to about 80 wt.-%, or about 30 to about 75 wt.-% of the total composition.

Among the fillers which can be used are non-reinforcing fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder. The non-reinforcing fillers can be surface treated. The surface treatment can generally be carried out with the same methods as described for the reinforcing fillers.

Suitable fillers also include reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than 50 µm.

A combination of reinforcing and non-reinforcing fillers can be desirable. In this respect, the quantity of reinforcing fillers may range from about 0.1 to about 15 wt.-%, in particular from about 1 to about 10 wt.-%. The difference in the named overall ranges, i.e. about 9 to about 80 wt.-%, can be accounted for by non-reinforcing fillers.

Pyrogenically-prepared, highly-disperse, silicic acids which can be hydrophobized by surface treatment are useful as reinforcing fillers. The surface treatment can be carried out, e.g. with dimethyldichlorosilane, hexamethyldisilazane, tetramethylcyclotetrasiloxane or polymethylsiloxane.

To control the reactivity of the addition reaction and to prevent premature curing, it may be advantageous to add an inhibitor (E) which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the invention and is herein incorporated by reference.

Examples of such inhibitors are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on an vinyl siloxane are 1,1,3,3-tetramethyl-1,3-divinyl siloxane and poly-, oligo- and disiloxanes containing vinyl groups.

The optional inhibitor can be present in an amount of up to about 0.3 wt.-% based on the composition, preferably in an amount of up to about 0.15 wt.-%.

Other optional additives (F) include those useful or advantageous for dental materials. For example, optional additives may include modifiers, dyes, pigments, thixotropic agents, flow improvers, polymeric thickeners, surfactants, odorous substances, diluting agent(s) and flavourings. Additives may be added alone or in admixture, and can be used to adjust the rheological characteristics.

The other optional additives can be present in an amount being in the range of about 0.05 to about 20 wt.-%, preferably in the range of about 0.1 to about 15 wt.-% with respect to the cured composition.

Thus, the inventive composition can comprise
component (A) in an amount in the range of about 1 wt.-% to about 95 wt.-%, or in an amount in the range of about 5 wt.-% to about 75 wt.-%, or in an amount in the range of about 10 wt.-% to about 60 wt.-%;
crosslinker component (B) in an amount in the range of about 1 wt.-% to about 80 wt.-% or in an amount in the range of about 5 wt.-% to about 50 wt.-%, or in an amount in the range of about 10 wt.-% to about 40 wt.-%;
catalyst component (C) in an amount of in the range of about 0.00005 wt.-% to about 0.05, wt.-%, or in an amount in the range of about 0.0002 wt.-% to about 0.04 wt.-%;
filler component (D) in an amount in the range of about 3.99995 wt.-% to about 90 wt.-% or in an amount in the range of about 19.9998 wt.-% to about 80 wt.-%, or in an amount in the range of about 29.9998 wt.-% to about 75 wt.-%;
optional inhibitor (E) in an amount in the range of about 0.001 wt.-% to about 0.3 wt.-%—or in an amount in the range of about 0.01 wt.-% to about 0.15 wt.-%;
optional additive (F) in an amount in the range of about 0.05 wt.-% to about 20 wt.-%—or in an amount in the range of about 0.1 wt.-% to about 15 wt.-%;
with respect to the cured composition.

Surprisingly it has been found that reacting component (A) with crosslinker component (B) results in hard materials, which are not brittle and have excellent physical properties, especially a high hardness. In a preferred embodiment, the composition cures to a hard product (e.g. having a detectable Shore hardness) under ambient conditions, e.g. at about 23° C. to about 25° C. within about 30 min or about 20 min or about 10 min.

It has also been found that the hard materials obtained show only negligible adhesion to silicone impression materials used in the dental field, even if the chemical basis of both the hard materials obtained when curing the inventive compounds and the silicone impression material are similar. This effect is especially advantageous using the inventive composition for the production of provisional crown and bridge materials. Having taken the impression of the dental situation with a silicone impression material the cured impression is hereinafter filled with a provisional crown and bridge material. In this respect the provisional crown or bridge material after curing should not show strong adhesion to the impression material.

When using the inventive composition for the production of a modelling material, the composition is poured into an impression to obtain a model of the dental situation of a patient. The situation can be compared to the above described procedure for obtaining a provisional crown and bridge material. The model material, after curing, should not show strong adhesion to the impression material, either.

A further surprising effect is that component (A) can have a relatively high content of unsaturated moieties in relation to its molecular weight, sometimes combined with relatively low viscosity.

Component (A) may be obtained by a standard hydrosilation reaction known to the skilled person using linear, multifunctional SiH containing siloxanes and organic molecules that comprise two or more carbon-carbon unsaturations that are of equivalent reactivity towards hydrosilation.

The synthesis of component (A) can be done e.g. by hydrosilation reaction of an at least bifunctional terminal unsaturated organic compound represented by formula (1)

wherein
A=linear or branched terminally unsaturated aliphatic residue (preferably comprising 2 to 20, or 3 to 10 C atoms), wherein the unsaturation is a C—C double bond not activated by a conjugated carbonyl group (e.g. vinyl, ethynyl, propynyl, allyl, butenyl, hexenyl, decenyl, p-ethenyl, styryl);
B=O, (O═)C—O, O—C(═O), O—C(═O)—O, NH, S (not conjugated to the unsaturation of A);
$C^{11}$=H or aliphatic, cycloaliphatic or aromatic organic or silicon organic residue comprising 1 to 50, or 1 to 35 C atoms and additionally up to 6 hetero atoms like O, N or S which can also be part of a ring system, being a-fold radically;
a=2, 3, 4, 5, 6, 7, 8, 9 or 10;
b=0 or 1 with an at least bifunctional hydrido silicone compound represented by formula (2):

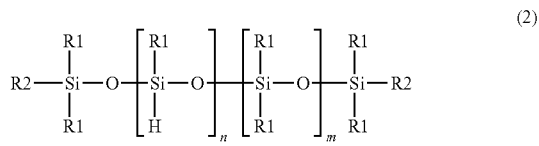

wherein
R1=alkyl, aryl or alkaryl each comprising 1 to 20 C atoms, wherein at least one of the H atoms can be substituted by halogen atoms (e.g. chlorine or fluorine) or alkyl groups (e.g. methyl, ethyl, propyl, butyl, phenyl or cyclohexyl);
R2=H, R1 or alkenyl with 1 to 10 C atoms, preferably H, methyl, vinyl, allyl or butenyl;
n=0 to 500, or 0 to 100, or 1 to 50;
m=0 to 500, or 0 to 100, or 1 to 50.

and optionally with a further unsaturated alky, aryl or alkaryl compound bearing only one unsaturated moiety and comprising 1 to 20 or 2 to 10 C atoms (e.g., ethylene, styrene, 1-hexene), wherein one, a part or all of the H atoms can be substituted by halogen atoms.

This reaction will lead to a preferred embodiment of component (A) which can be represented by formula (3):

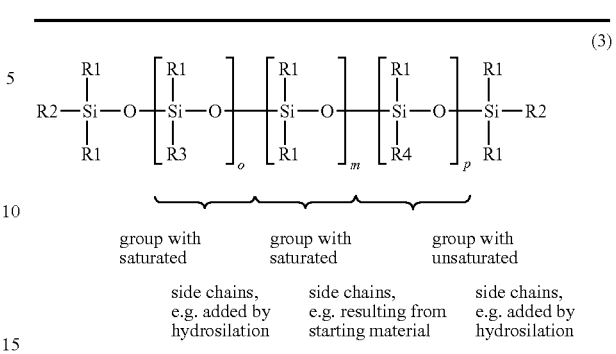

wherein:
R1=alkyl, aryl or alkaryl each comprising 1 to 20 carbon atoms, preferably 1 to 10 carbon atoms, wherein one or more (and sometimes all) of the carbon atoms can be substituted with halogen atoms (e.g., fluorine or chlorine) or alkyl groups (e.g. methyl, ethyl, propyl, butyl, phenyl or cyclohexyl);
R2=is either equal to R1 or, in the case where p is 0, R4;
R3=alkyl, aryl or alkaryl group comprising 1 to 20 carbon atoms, wherein at least one of the H atoms can be substituted by halogen atoms, preferably ethyl, hexyl, octyl decyl, 2-phenylethyl, dodecyl, tetradecyl, hexadecyl or octadecyl;
R4=linear or branched, terminally unsaturated aliphatic, cycloaliphatic or aromatic organic or silicon organic residue moiety having (a−1) ethylenic unsaturations, wherein a is as defined above, and wherein such unsaturations are carbon-carbon double bonds not activated by a conjugated carbonyl group (e.g., vinyl, ethynyl, propynyl, allyl, 3-butenyl, 5-hexenyl, 9-decenyl, p-ethenyl-styryl), wherein the moiety comprises preferably 1 to 50 carbon atoms, or 5 to 30 carbon atoms, and additionally up to 6 oxygen atoms which can also be part of a ring system;
o=0 to 12, or 0 to 8, or 0 to 5, or 0 to 2;
m=0 to 50, or 0 to 35, or 0 to 20, or 0 to 10;
p=0 to 500, or 1 to 100, or 2 to 75, or 5 to 50.

Preferably (o+m+p) is about 0 to 500, or 1 to 100, or 2 to 75, or 5 to 50.

During hydrosilation, unsaturated compound (1) reacts with the SiH moiety of compound (2) and turns into R4. The reaction usually results in a mixture of the α- and the β-adduct. The formulas used in the description always show the β-adduct. However, the α-adduct may also be present.

In this respect it should be mentioned that the compound according to formula (3) is idealized in that it only shows the reaction product of compounds according to formula (1) with compounds according to formula (2), whereas both compounds are oligofunctional. Without wishing to be limited to any particular mechanism, it is assumed that a minor crosslinking reaction takes place not shown in the formulas. Surprisingly, it has been found that the assumed crosslinking reaction does not result in a significant thickening or gelling of the resulting compounds. The resulting compounds remain capable of flowing.

Although the extent of chain extension during this reaction—due to reaction of any remaining unsaturation in R4 with a second silicone chain—is so low that the products obtained have a relatively low viscosity, chain extension may still occur to a certain amount. This may be illustrated by the example given in the formula below.

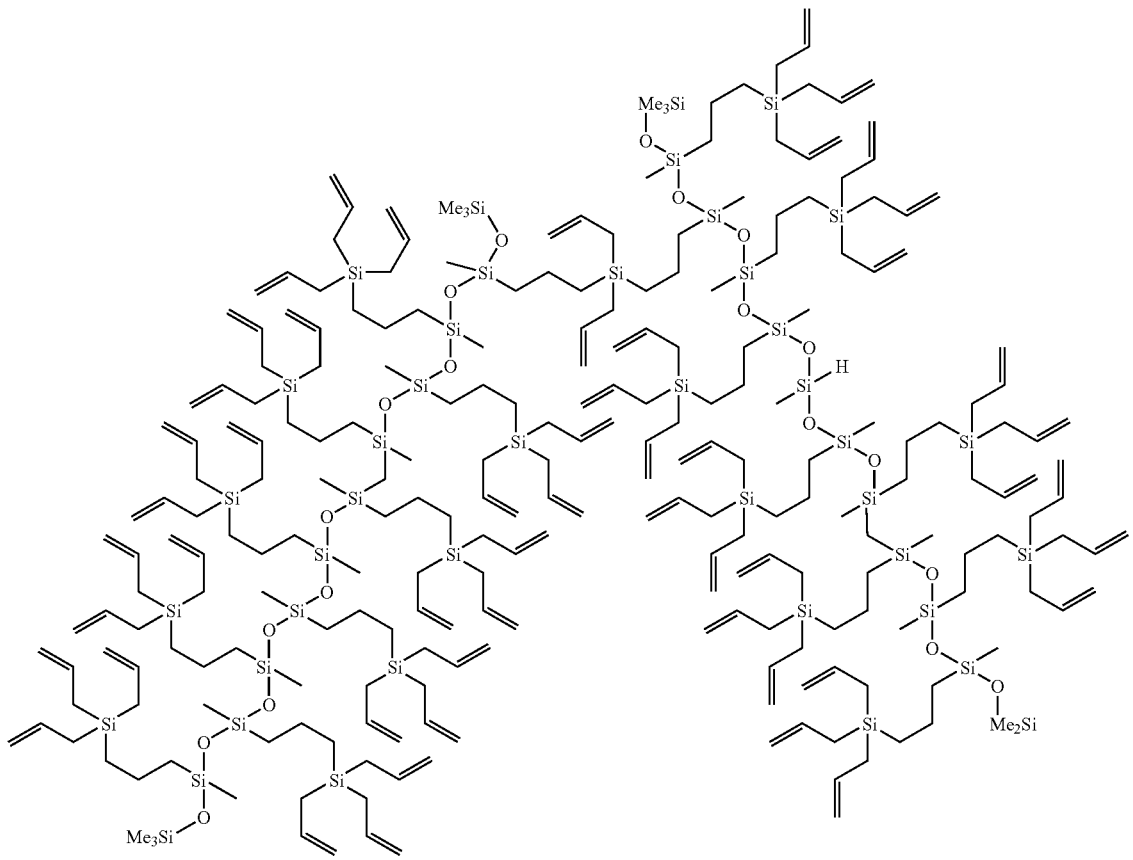

What can also be taken from this example is, that residual SiH groups may remain in the molecule. It can also be calculated by stoichiometry, that only a fraction of the initial SiH content of the compound according to formula (2) reacts with compounds according to formula (1). The rest can be saturated, if desired, by addition of, and hydrosilation with optionally unsaturated compounds containing alkyl, aryl or alkaryl residues mentioned above (e.g. ethylene, styrene, hexene) to give residue R3 at the given silicon atom. A fraction of 0 up to 25% of the initial SiH residues in the chain may be saturated in this way.

Compounds according to formula (3) can also be obtained via a different way. For example, suitable dihalogen- or dialkoxysilanes or the corresponding mixture of such silanes can be hydrolysed combined with subsequent condensation in the presence of suitable chain-terminating groups.

In one embodiment, one may react compounds according to formula (1), for example, with dichlormethylsilane using a standard hydrosilation reaction. The product obtained might then be hydrolysed and condensed in the presence of hexamethyldisiloxane. This will also result in compounds according to formula (3). The hydrolysis and condensation can also be conducted in the presence of a silane, like methyl-phenyldichlorosilane.

The preparation of corresponding molecules can be achieved, e.g., according to standard procedures which are portrayed in W. Noll, "Chemie und Technologie der Silikone", Verlag Chemie Weinheim 2nd edition 1968, pages 162-206 or J. Burghardt, Chemie und Technologie der Polysiloxane in "Silikone, Chemie und Technologie", Vulkan Verlag, Essen, 1989, pages 23-37.

Surprisingly, for linear siloxanes, and in contrast to many cyclic siloxanes, the hydrosilation reaction does not lead to an unacceptable increase of viscosity or gelation of the polymer to such an extent that it is not useful in dental formulations. Thus, the invention is also directed to the product obtainable by reacting compound (1) with compound (2) as defined above.

Representative compounds according to formula (1) include di-, tri- or higher unsaturated functionality. A functionality of unsaturation of about 2 to about 10 is preferred, although about 2 to about 6 can be even more preferred.

The compounds according to formula (1) may be further characterized by the term equivalent weight as defined above. The compounds according to formula (1) generally have an (EW) varying between about 27 g/mole and about 500 g/mole, or between about 34 g/mole and about 350 g/mole. The molecular weight of compound (1) can be in the range of about 54 g/mole to about 1000 g/mole, or about 68 g/mole to about 800 g/mole.

Examples of useful compounds according to formula (1) are:
Diallylether (A=Vinyl, a=2, b=0, C=2-Oxo-propane-1,3-diyl);
Diallylcarbonate (A=Allyl, a=2, b=1, B=O, C=Carbonyl);
Ethyleneglycoldiallylcarbonate (A=Allyl, a=2, b=1, B=O, C=1,2-Bis-(carbonyloxy)ethane);
Diethyleneglycoldiallylcarbonate (A=Allyl, a=2, b=1, B=O, C=Bis-(carbonyloxyethyl)ether);

Pentaerythritol-tetraallylether (A=Allyl, a=4, b=1, B=O, C=Tetrakis-(methylene)-methane);
Di-Pentaerythritol-hexaallylether (A=Allyl, a=6, b=1, B=O, C=Bis-[tetra-(methylene)-methane)ether;
Trimethylolethane-triallylether (A=Allyl, a=3, b=1, B=O, C=Methyl-tris-(methylene)-methane);
Trimethylolpropane-triallylether (A=Allyl, a=3, b=1, B=O, C=Ethyl-tris-(methylene)-methane);
Ethyleneglycol-diallylether (A=Allyl, a=2, b=1, B=O, C=Ethane-1,2-diyl);
Diethyleneglycoldiallylether (A=Allyl, a=2, b=1, B=O, C=3-Oxa-pentane-1,5-diyl);
1,2-Propanedioldiallylether (A=Allyl, a=2, b=1, B=O, C=Propane-1,2-diyl);
1,3-Propanedioldiallylether (A=Allyl, a=2, b=1, B=O, C=Propane-1,3-diyl);
1,3-Butanedioldiallylether (A=Allyl, a=2, b=1, B=O, C=Butane-1,3-diyl);
1,4-Butanedioldiallylether (A=Allyl, a=2, b=1, B=O, C=Butane-1,4-diyl);
1,4-Butenedioldiallylether (A=Allyl, a=2, b=1, B=O, C=Butene-1,4-diyl);
1,4-Butynedioldiallylether (A=Allyl, a=2, b=1, B=O, C=Butyne-1,4-diyl);
1,5-Pentanedioldiallylether (A=Allyl, a=2, b=1, B=O, C=Pentane-1,5-diyl);
1,6-Hexanedioldiallylether (A=Allyl, a=2, b=1, B=O, C=Hexane-1,6-diyl);
1,8-Octanedioldiallylether (A=Allyl, a=2, b=1, B=O, C=Octane-1,8-diyl);
1,9-Nonanedioldiallylether (A=Allyl, a=2, b=1, B=O, C=Nonane-1,9-diyl);
1,10-Decandioldiallylether (A=Allyl, a=2, b=1, B=O, C=Decan-1,10-diyl);
1,12-Dodecanedioldiallylether (A=Allyl, a=2, b=1, B=O, C=Dodecane-1,12-diyl)
Glycerol-triallylether (A=Allyl, a=4, b=1, B=O, C=Propane-1,2,3-triyl);
1,2,4-Butanetrioltriallylether (A=Allyl, a=3, b=1, B=O, C=Butane-1,2,4-triyl);
1,2,6-Hexanetrioltriallylether (A=Allyl, a=3, b=1, B=O, C=Hexane-1,2,4-triyl);
Diglyceriol-tetraallylether (A=Allyl, a=4, b=1, B=O, C=4-Oxa-heptane-1,2,6,7-tetryl);
Erythritol-tetraallylether (A=Allyl, a=4, b=1, B=O, C=Butane-1,2,3,4-tetryl);
Mannite-hexaallylether (A=Allyl, a=6, b=1, B=O, C=Hexane-1,2,3,4,5,6-hexyl);
Sorbitol-hexaallylether (A=Allyl, a=6, b=1, B=O, C=Hexane-1,2,3,4,5,6-hexyl);
Inositol-hexaallylether (A=Allyl, a=6, b=1, B=O, C=Cyclohexane-1,2,3,4,5,6-hexyl);
Oxalic acid diallylester (A=Allyl, a=2, b=1, B=O, C=Ethanedione);
Malonic acid diallylester (A=Allyl, a=2, b=1, B=O, C=1,3-Propanedione);
Succinic acid diallylester (A=Allyl, a=2, b=1, B=O, C=1,4-Butanedione);
Adipic acid diallylether (A=Allyl, a=2, b=1, B=O, C=1,6-Hexanedione);
Sebacic acid diallylether (A=Allyl, a=2, b=1, B=O, C=1,8-Octanedione);
"Santolink XI 100" (from Monsanto) (polymeric A=Allyl, a=1-20, b=1, B=O, C=oligomeric backbone of 2-(methylene)ethyloxy repetition units);
Dimethyldiallylsilane (A=Vinyl, a=2, b=0, C=2-Dimethylsilyl-1,3-propanediyl);
Divinyldimethylsilane (A=Vinyl, a=2, b=0, C=Dimethylsilanediyl);
Diphenyldiallylsilane (A=Vinyl, a=2, b=0, C=2-Diphenylsilyl-1,3-propanediyl);
Diphenyldivinylsilane (A=Vinyl, a=2, b=0, C=Diphenylsilanediyl);
Triallylmethylsilane (A=Vinyl, a=3, b=0, C=Methyl-tris-(methylene)-silane);
Trivinylmethylsilane (A=Vinyl, a=3, b=0, C=Methylsilanetriyl);
Tetraallylsilane (A=Vinyl, a=4, b=0, C=Tetrakis-(methylene)-silane);
Tetravinylsilane (A=Vinyl, a=4, b=0, C=Silanetetryl);
Bis-(4-allyloxyphenyl)-sulfone (A=Allyl, a=2, b=1, B=O, C=Bis-(p-phenylene)-sulfon); $C_{18}H_{18}O_2S$; EW=149 g/mole
Bis-(4-allyloxyphenyl)-keton (A=Allyl, a=2, b=1, B=O, C=Bis-(p-phenylene)-ketone); $C_{19}H_{18}O_3$; EW=147 g/mole
Bis-(4-allyloxyphenyl)-methane (A=Allyl, a=2, b=1, B=O, C=Bis-(p-phenylene)-methane); $C_{19}H_{20}O_2$; EW=140 g/mole
1,1-Bis-(4-allyloxyphenyl)-ethane (A=Allyl, a=2, b=1, B=O, C=1,1-Bis-(p-phenylene)-ethane);
2,2-Bis-(4-allyloxyphenyl)-propane (A=Allyl, a=2, b=1, B=O, C=2,2-Bis-(p-phenylene)-propane); $C_{21}H_{24}O_2$; EW=154 g/mole
2,2-Bis-(4-allyloxyphenyl)-perfluoropropane (A=Allyl, a=2, b=1, B=O, C=2,2-Bis-(p-phenylene)-perfluoropropane); $C_{21}H_{18}F_6O_2$; EW=208 g/mole
2,2-Bis-(4-allyloxy-3,5-dibromo-phenyl)-propane (A=Allyl, a=2, b=1, B=O, C=2,2-Bis-(4-phenylene-3,5-dibromo)-propane); $C_{21}H_{20}Br_4O_2$; EW=312 g/mole
3,3-Bis-(4-allyloxyphenyl)-pentane (A=Allyl, a=2, b=1, B=O, C=3,3-Bis-(p-phenylene)-pentane);
4,4-Bis-(4-allyloxyphenyl)-heptane (A=Allyl, a=2, b=1, B=O, C=2,2-Bis-(p-phenylene)-heptane); $C_{25}H_{32}O_2$; EW=182 g/mole
1,1-Bis-(4-allyloxyphenyl)-cyclopentane (A=Allyl, a=2, b=1, B=O, C=1,1-Bis-(p-phenylene)-cyclopentane); $C_{23}H_{26}O_2$; EW=167 g/mole
1,1-Bis-(4-allyloxyphenyl)-cyclohexane (A=Allyl, a=2, b=1, B=O, C=1,1-Bis-(p-phenylene)-cyclohexane); $C_{24}H_{28}O_2$; EW=174 g/mole
1,1-Bis-(4-allyloxyphenyl)-3,3,5-trimethylcyclohexane (A=Allyl, a=2, b=1, B=O, C=1,1-Bis-(p-phenylene)-3,3,5-trimethylcyclohexane); $C_{27}H_{34}O_2$; EW=195 g/mole
1,1,1-Tris-(4-allyloxyphenyl)-ethane (A=Allyl, a=3, b=1, B=O, C=1,1,1-Tris-(p-phenylene)-ethane);
Bis-(allyloxy)-tricyclo[5.2.1.0$^{2.6}$]decane (A=Allyl, a=2, b=1, B=O, C=tricyclo[5.2.1.0$^{2.6}$]decane).

Many suitable bifunctional hydrido silicone compounds according to formula (2) are known in the art.

Representative compounds according to formula (2) can comprise terminal and/or pendant SiH groups. Compound (2) can be defined as a molecule only in the case of disiloxane (R2=H, n=m=0). Otherwise it is a silicone polymer with a chain length distribution and polydispersity typical for silicone polymers (Encyclopedia of Polymer Science and Engeneering 2$^{nd}$ Edition, Vol 15 pages 204-308).

Typically, the siloxane polymers have pendant or terminal SiH functionality. In some cases, especially for siloxane polymers having a low molecular weight both can be the case. A silicon atom usually does not have more than one SiH functional group but there can be silicon atoms with no SiH function like in terminal functional silicones, with all non-terminal silicon atoms, and in pendant functional silicone copolymers with the co-monomer being not SiH functional.

The average chain length (m+n+2)—according to formula (2)—of such silicone polymer samples generally is low and does usually not exceed about 500 Si-atoms, can sometimes be lower than about 100 Si-atoms sometimes can be lower than about 75 Si-atoms or can be in the range of about 5 to about 50 Si-atoms. The average number of SiH groups in such polymers will usually not exceed about 50 SiH-groups, sometimes not exceed about 35 SiH-groups, sometimes not exceed about 20 SiH-groups or sometimes not exceed about 10 SiH groups. In terminal functional siloxanes or silicone polymers the SiH functionality can be as low as 2.

The average $M_n$ of compound (2) usually does not exceed about 20000 g/mole, preferably does not exceed 10000 g/mole. The average $M_n$ of compound (2) can be up to or below about 8000 g/mole.

Examples of useful compounds according to formula (2) are:

Methylhydrogensiloxane-Polymers with Trimethylsiloxy-Endgroups (R1=Methyl, R2=Methyl, n=100% von (n+m), $\emptyset_{(n+m)}$<50); $M_n$<3200 g/mole Methylhydrogensiloxane-Polymers with Dimethylhydrogensiloxy-Endgroups (R1=Methyl, R2=H, n=100% von (n+m), $\emptyset_{(n+m)}$<50); $M_n$<3200 g/mole Methylhydrogensiloxane-co-Dimethylsiloxane-Copolymers with Trimethylsiloxy-Endgroups (R1=Methyl, R2=Methyl, 20%<n<70% von (n+m), $\emptyset_{(n+m)}$<50); $M_n$<3700 g/mole Methylhydrogensiloxane-co-Dimethylsiloxane-Copolymers with Dimethylhydrogensiloxy-Endgroups (R1=Methyl, R2=H, 20%<n<70% von (n+m), $\emptyset_{(n+m)}$<50); $M_n$<3700 g/mole Phenylhydrogensiloxane-Polymers with Trimethylsiloxy-Endgroups (R1=Phenyl bzw. Methyl, R2=Methyl, n=100% von (n+m), $\emptyset_{(n+m)}$<50); $M_n$<6300 g/mole Phenylhydrogensiloxane-Polymers with Dimethylhydrogensiloxy-Endgroups (R1=Phenyl bzw. Methyl, R2=H, n=100% von (n+m), $\emptyset_{(n+m)}$<50); $M_n$<6300 g/mole Phenylhydrogensiloxane-co-Dimethylsiloxane-Copolymers with Trimethylsiloxy-Endgroups (R1=Phenyl bzw. Methyl, R2=Methyl, 20%<n<70% von (n+m), $\emptyset_{(n+m)}$<50); $M_n$<5600 g/mole Phenylhydrogensiloxane-co-Dimethylsiloxane-Copolymers with Dimethylhydrogensiloxy-Endgroups (R1=Phenyl bzw. Methyl, R2=H, 20%<n<70% von (n+m), $\emptyset_{(n+m)}$<50); $M_n$<5600 g/mole Methylhydrogensiloxane-co-Phenylmethylsiloxane-Copolymers with Trimethylsiloxy-Endgroups (R1=Methyl bzw. Phenyl, R2=Methyl, 20%<n<70% von (n+m), $\emptyset_{(n+m)}$<50); $M_n$<5700 g/mole Methylhydrogensiloxane-co-Phenylmethylsiloxane-Copolymers with Dimethylhydrogensiloxy-Endgroups (R1=Methyl bzw. Phenyl, R2=H, 20%<n<70% von (n+m), $\emptyset_{(n+m)}$<50); $M_n$<5700 g/mole Dimethylsiloxane-Polymers with Dimethylhydrogensiloxy-Endgroups (R1=Methyl, R2=H, m=100% von (n+m), $\emptyset_{(n+m)}$<10); $M_n$<900 g/mole Diphenylsiloxane-Polymers with Dimethylhydrogensiloxy-Endgroups (R1=Phenyl bzw. Methyl, R2=H, m=100% von (n+m), $\emptyset_{(n+m)}$<10); $M_n$<2100 g/mole Phenylmethylsiloxane-Polymers with Dimethylhydrogensiloxy-Endgroups (R1=Methyl bzw. Phenyl, R2=H, m=100% von (n+m), $\emptyset_{(n+m)}$<10); $M_n$<1440 g/mole.

The curable compositions of the invention are usually pre-mixed into two or more parts prior to use. For example, one part may contain component (A) and catalyst (C), e.g. a platinum containing catalyst, while a second part may contain crosslinker component (B) and optionally other unsaturated containing organopolysiloxanes such as polydimethylsiloxanes with terminal dimethyl-vinyl-siloxy-groups.

Therefore, the invention also relates to a kit of parts, comprising a base part (I) and a catalyst part (II), wherein the base part (I) comprises components (A) and (B), and the catalyst part (II) comprises component (C), and wherein component (D) is present either in the base part or the catalyst part or in the base part and the catalyst part. The other optional component(s) (E) and (F) can be present either in the base part or the catalyst part or in the base part and the catalyst part.

The invention also relates to a method of producing a curable composition comprising the steps i) providing components (A), (B), (C), (D) and optionally (E) and (F), ii) mixing the components.

The dosing of the components can be carried out by sight (strand-length comparison), by weight, via pre-dosed pack units and subsequent manual mixing, from double-chambered cartridges with static mixing tubes or by means of volume dosing systems with downstream static or dynamic mixers.

Due to the low viscosity of component (A) and the absence of a smear layer component (A) is especially useful for producing hard materials, for examples coatings, varnishes, plastics and dental materials.

The term "dental materials" comprises filling materials (provisional and permanent), cements, provisional crown and bridge materials, modelling materials, bite registration materials, and materials used in the prosthodontic field.

If used in the dental field, the composition can be applied using e.g. the following steps: providing the components of the composition, mixing the components, applying the composition to a surface, letting the composition cure.

The surface can be the surface of soft or hard oral tissue, the surface of an impression material, preferably of a cured impression material, the surface of a crown or the surface of a model of a tooth stump.

The invention is hereinafter described by examples without limiting the scope of the invention.

EXAMPLES

Measurements

The measurements were done at standard temperature and pressure ("STP", i.e. 25° C. and 1023 hPas) according to the methods described below. The measurements were performed on the basis of specimens obtained after mixing the respective basis and catalyst pastes, curing the composition for one hour at room temperature and hereinafter storing the cured composition for 23 hours at 36° C. in water.

The compressive strength was measured according to ISO 7489. Cylindrical specimens (height 8 mm, diameter 4 mm) were tested using a Zwick Universal Testing Machine Z 010 (speed 4 mm/min, force 10 N, speed 10 mm/min).

The flexural strength was determined according to DIN 51048 using (cuboid specimen, height 4 mm, width 6 mm, length 25 mm, span 20 mm, speed 2 mm/min).

The E-modulus was determined using the measurement of flexural strength between 20 and 50% of $F_{max}$ according to the following formula:

$$E = [IV^3/(4 \cdot b \cdot h^3)] \cdot [(XH-XL)/\Delta L]$$

wherein:
E=E-Modulus [N/mm³]
IV=span [mm]

b=width of the specimen
h=height of the specimen
XH=upper point of the determination of the E-Modulus
XL=lower point of the determination of the E-Modulus
ΔL=bending value between XH and XL [mm]

The tensile strength was determined according to DIN 53455 using a Zwick Universal Testing Machine Typ 1455. Slightly modified specimens were used (l=25 mm; b=2 mm; h=2 mm; speed=2 mm/min).

The impact strength was determined according to DIN 53453 using a Zwick impact testing machine 5113 with a 0.5 J pendulum (width of indented specimen 6 mm, height 4 mm, length 50 mm).

The viscosity can be measured with a Haake Rotovisco RV20 device (spindle MV, measuring cup NV). the viscosity was measured at 23° C. After activation and rectification of the system, spindle MV was installed. Following, the material to be measured was filled into the measuring cup NV. Without undue delay, the spindle was lowered into the measuring cup NV. The spindle should be covered by a layer of max. 1 mm. The material to be measured was tempered for 20 min at 23° C. The measurement was started and the viscosity values (mPas) were recorded starting 20 s after the start of measurement. It has to be taken care of that at no time the measuring cup NV itself may rotate or move at all. A value for the viscosity was obtained in mPa*s. The above mentioned method of measurement corresponds to DIN 53018-1.

The shore hardness D of the cured composition of the invention was measured according to DIN 53505 with a durometer (specimen: disc with a diameter of 38 mm and a height of 6 mm; measurement taken 24 h after mixing the components).

The molecular weight ($M_w$) was determined with gel permeation chromatography (GPC). Calibration was done using commercially available polystyrol (PS) samples with narrow molecular weight distributions. Appropriate methods are known by the expert as described in "Polymer Analysis", Barbara Stuart, John Wiley (ISBN 0471899267 (Hb),_pages 108 to 112. In addition the determination of the molecular weight can be done using nuclear magnetic resonance spectroscopy (end-group determination).

If not indicated otherwise, all chemical compounds used are commercially available from Aldrich, Fluka, Acros, ABCR or Gelest.

Example 1

Synthesis of a Component (A) Using a H-Siloxane and Pentaerythritol Tetraallylether

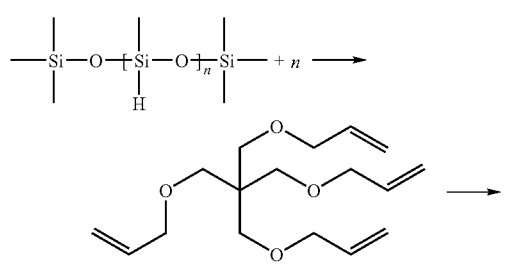

-continued

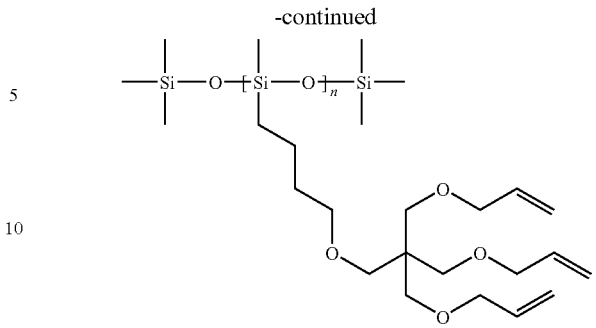

16.6 g Pentaerythritol-tetraallylether [M=280.45; 0.059 Mole] were added to a heated mixture of 5 g of a Methylhydridosilicone oil [M=550; n=6.5; 0.0091 Mole], 60 mg 5% platinum on carbon and 10 ml of toluene such that no hydrogen evolution was observed. The reaction mixture was stirred until the SiH-absorption in the IR-Spectrum located at about 2100 $cm^{-1}$ had disappeared. After workup and isolation of the product 20.5 g of a clear colorless oil was obtained with an (EW) of 130 g/mole.

Example 2

Synthesis of a Component (A) Using a H-Siloxane and Tetraallylsilane

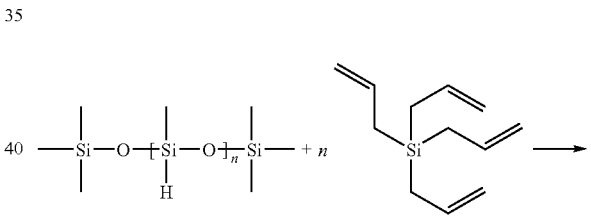

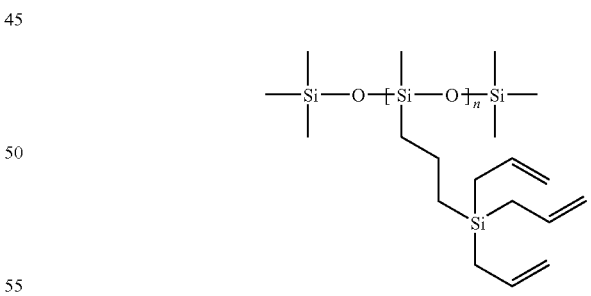

24.9 g Tetraallylsilane [M=192.38; 0.13 Mole] were added to a heated mixture of 10 g of a Methylhydridosilicone oil [M=2470; n=32; 4.05 mMole], 120 mg 5% platinum on carbon and 20 ml of tolulene such that no hydrogen evolution was observed. The reaction mixture was stirred until the SiH-absorption in the IR-Spectrum located at about 2100 $cm^{-1}$ had disappeared. After workup and isolation of the product 33.5 g of a clear colorless and viscous oil was obtained with an (EW) of 93 g/mole.

Example 3

3. a) Synthesis of Component (A) Using a H-Siloxane and Tetraallylsilane

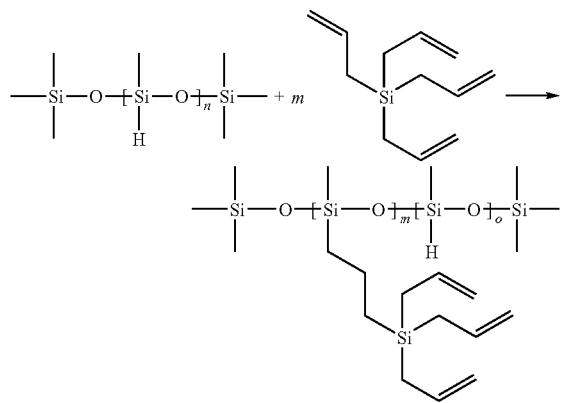

12.45 g Tetraallylsilane [M=192.38; 0.13 Mole] were added to a heated mixture of 10 g of a Methylhydridosilicone oil [M=2470; n=32; 4.05 mMole], 120 mg 5% platinum on carbon and 20 ml of toluene such that no hydrogen evolution was observed. The reaction mixture was stirred until the SiH-absorption in the IR-Spectrum located at about 2100 cm$^{-1}$ was constant.

3. b) Synthesis of Component (A) Using the Compound Obtained in Example 3 a) and Styrene

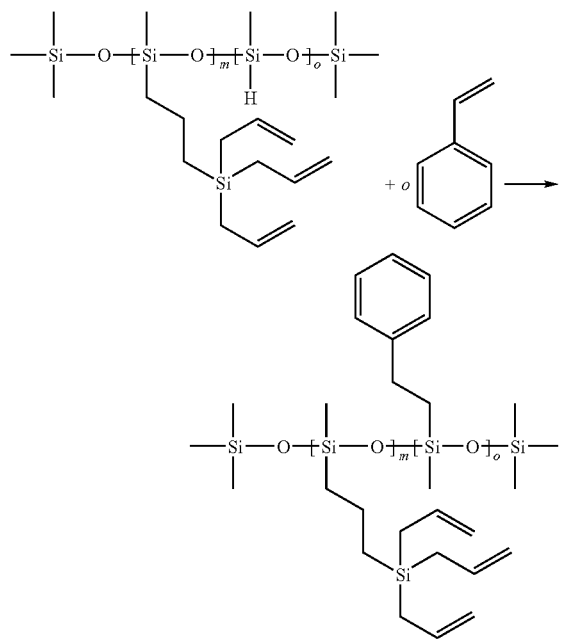

Thereafter to the reaction mixture of 3. a) 6.8 g of styrene [M=104.15; 0.065 M] were added slowly. The reaction mixture was stirred until the SiH-absorption in the IR-Spectrum located at about 2100 cm$^{-1}$ had disappeared. After workup and isolation of the product 27.5 g of a clear colourless and viscous oil was obtained with an (EW) of 160 g/mole.

Example 4

Synthesis of Component (A) Using 1,1,3,3-Tetramethyldisiloxane and Tetraallylsilane

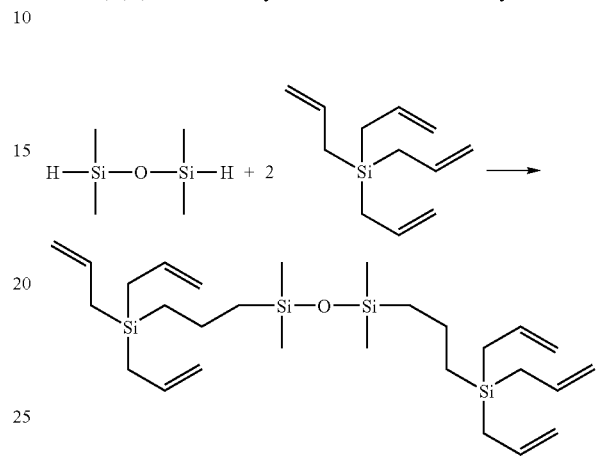

5 g Tetramethyldisiloxane, 50 ml Toluene, 64.1 mg Pt on Carbon (10% Pt), 12.8 mg Brenzcatechine and 12.8 mg Al-Cupfferone were placed in a round bottom flask and heated to reflux. 16.9 g Tetraallylsilane (92.6% pure) were added drop-wise. Reflux was continued until SiH-band in IR spectrum at ~2100 cm$^{-1}$ vanished. After filtration and workup 15.6 g of a clear yellow liquid remained with no residual SiH and a (EW) of 93 was obtained.

Example 5

Synthesis of Component (A) Using Poly(Hydrogene Methyl)Siloxane and Bisphenole A Diallylether

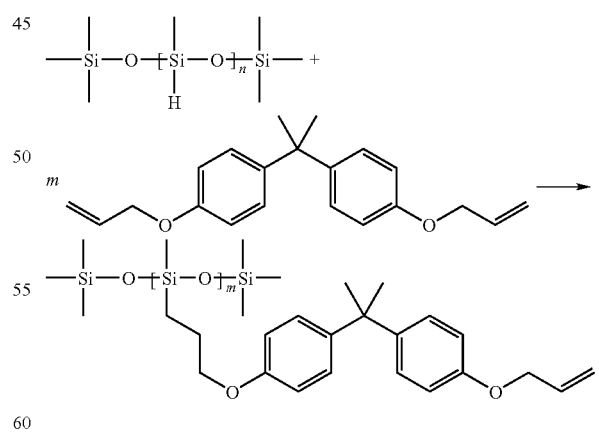

10 g Poly(hydrogene methyl)siloxane (100% n, n~7), 150 ml Toluene, 191.5 mg Pt on Carbon (10% Pt), 38.3 mg Brenzcatechine and 38.3 mg Al-Cupferrone were placed in a round bottom flask and heated to reflux. 51.4 g Bisphenole A diallylether were added drop-wise. Reflux was continued until SiH-band in IR spectum at ~2100 cm$^{-1}$ no longer decreased.

After workup 60 g of a yellow liquid was obtained. Viscosity: 0.77 Pa*s, (EW) of 266 g/mole.

Example 6

Synthesis of Component (A) Using Poly(Hydrogene Methyl)Siloxane and 1,5-Hexadiene

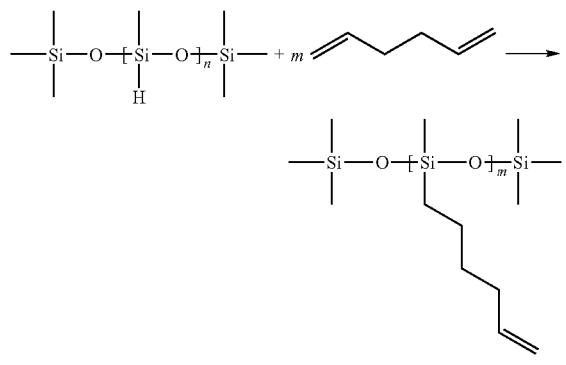

20 g Poly(hydrogene methyl)siloxane (100% n, n~7), 175 ml Toluene, 199.1 mg Pt on Carbon (10% Pt), 199 mg Methoxyphenole and 199 mg Ionol were placed in a round bottom flask and heated to reflux. 28 g 1,5-Hexadiene (98%) were added dropwise. Reflux was continued until SiH-band in IR spectum at ~2100 cm$^{-1}$ no longer decreased. After workup 32.1 g of a yellow liquid was obtained; (EW) of 284 g/mole.

Example 7

Synthesis of a Crosslinker Component (B) According to 1st Example of Preparation of U.S. Pat. No. 5,086,148

7 mg of hexachloroplatinic acid was introduced into 7.92 g of (20 mMole) bisphenol-A-bisallyloxyethylether and the mixture was stirred for 15 minutes at ambient temperature, until the majority of the hexachloroplatinic acid was dissolved. Following this 9.6 g of (40 mMole). Tetramethylcyclotetrasiloxane was added drop-wise at ambient temperature. Within 20 minutes the temperature of the mixture rose to 55° C. Stirring was continued until the mixture had cooled to a temperature of 30° C. Stirring was continued for additional 2 hours. Finally, filtration with silica gel removed a small amount of a black precipitate and 10 g of compound B was obtained. NMR-spectroscopic characterisation showed that the broad multiplett of the allyl group between 5.0 and 6.3 ppm had disappeared. In the infrared spectrum the SiH-group of the product was at 2168 cm$^{-1}$.

Examples of Use

Example of Use 1

Using a standard laboratory mixer a base paste 1 was prepared under vacuum. The following components (weight percent in the mix) were mixed to homogeneity.

Base Paste 1

| Component | amount = weight-% |
| --- | --- |
| Component (A) of Example 5 | 10.0 g = 31.8 wt.-% |
| Component (B) of Example 7 | 10.0 g = 31.8 wt.-% |
| Polydimethylsiloxane, trimethylsiloxyterminated ($\eta$ = 10 mPa * s) | 1.0 g = 3.2 wt.-% |
| Pyrogenic silica Aerosil R 202 | 0.5 g = 1.6 wt.-% |
| Cristobalit-Filler (BET = 3 m$^2$/g) | 10.0 g = 31.6 wt.-% |

20 mg of a solution of a platinum-tetramethyl-divinyldisiloxane complex in silicone oil (1.3 weight-% platinum) were added to this paste by stirring. After 1 minute setting reaction started. After 6.5 minutes setting was complete resulting in a hard product. Shore hardness D according to DIN 53505 was 73 measured 10 minutes after mixing.

Example of Use 2

A base paste 2 and catalyst paste 2 were prepared using a standard laboratory mixer under vacuum. The components below were mixed to homogeneity. Data down below show the components and their amount in gram as well as the resulting weight percent share in the formulation of the paste.

Base Paste 2

| Component | amount = weight-% |
| --- | --- |
| Component (B) of Example 7 | 31.7 g = 45.4 wt.-% |
| Polydimethylsiloxane, trimethylsiloxy terminated ($\eta$ = 10 mPa * s) | 1.6 g = 2.3 wt.-% |
| Pyrogenic silica Aerosil R 202 | 0.8 g = 1.1 wt.-% |
| Cristobalit-Filler (BET = 3 m$^2$/g) | 35.6 g = 51.1 wt.-% |

Catalyst Paste 2

| Component | amount = weight-% |
| --- | --- |
| Component (A) of Example 2 | 8.6 g = 43.0 wt.-% |
| Polydimethylsiloxane, trimethylsiloxy terminated ($\eta$ = 10 mPa * s) | 0.1 g = 0.4 wt.-% |
| Pyrogenic silica Aerosil R 202 | 1.6 g = 11.7 wt.-% |
| Cristobalit-Filler (BET = 3 m$^2$/g) | 9.4 g = 43.0 wt.-% |
| Catalyst (C) | 0.4 g = 1.9 wt.-% |

Platinum-Tetramethyl-Divinyldisiloxane-Complex in Silicone Oil (1.3 Weight-% Platinum Metal)

Base paste 2 and catalyst paste 2 were filled into standard cartridges and were mixed by pressing through a static mixing tip at a volume ratio of base:catalyst=4:1. After 25 seconds setting reaction started indicated by an increase of viscosity and temperature of the mixture. This setting reaction was finished after 1.5 minutes. The result was a hard product having a shore hardness D of 63 measured 24 h after mixing.

Example of Use 3

A base paste 3 and catalyst paste 3 were prepared using a standard laboratory mixer under vacuum. Components as to be seen down below were mixed to homogeneity. Data below show the components and their amount in gram as well as the resulting weight percent share in the formulation of the paste.

Base Paste 3

| Component | amount = weight-% |
|---|---|
| Component (B) of Example 7 | 31.7 g = 45.5 wt.-% |
| Polydimethylsiloxane, trimethylsiloxy terminated ($\eta$ = 10 mPa * s) | 1.6 g = 2.3 wt.-% |
| Pyrogenic silica Aerosil R 202 | 0.8 g = 1.1 wt.-% |
| Cristobalit-Filler (BET = 3 m$^2$/g) | 35.6 g = 51.1 wt.-% |

Catalyst Paste 3

| Component | amount = weight-% |
|---|---|
| Component (A) of Example 5 | 31.6 g = 44.3 wt.-% |
| Polydimethylsiloxane, trimethylsiloxy terminated ($\eta$ = 10 mPa * s) | 1.6 g = 2.2 wt.-% |
| Pyrogenic silica Aerosil R 202 | 0.8 g = 1.1 wt.-% |
| Cristobalit-Filler (BET = 3 m$^2$/g) | 35.8 g = 50.2 wt.-% |
| Catalyst (C) | 1.6 g = 2.2 wt.-% |

Platinum-Tetramethyl-Divinyldisiloxane-Complex in Silicone Oil (1.3 Weight-% Platinum Metal)

Base paste 3 and catalyst paste 3 were filled into standard cartridges and were mixed by pressing through a static mixing tipp with a volume ratio of base:catalyst=1:1. After 1.5 minutes setting reaction started indicated by an increase of viscosity and temperature of the mixture. This setting reaction was finished after 3.5 minutes. The result was a hard product having the following characteristics.

| Compressive Strength | 120 MPa |
|---|---|
| Flexural Strength | 70 MPa |
| E-Modulus | 2390 MPa |
| Tensile Strength | 32 MPa |
| Impact Strength | 9.4 kJ/m$^2$ |
| Shore hardness D | 77 |

The mixed paste could be applied directly into set impressions of a patient's mouth based on alginates, addition cured (e.g. Position® Penta®, 3M ESPE AG, Seefeld), or condensation cured silicone impression materials. After setting the material could be easily removed from the impressions. Because of that the material could be used as a model material to prepare dental casts from dental impressions and as a product for the preparation of provisional crowns and bridges.

Example of Use 4

A base paste 4 and catalyst paste 4 were prepared using a standard laboratory mixer under vacuum. The components below were mixed to homogeneity. Data below show the components and their amount in gram as well as the resulting weight percent share in the formulation of the paste.

Base Paste 4

| Component | amount = weight-% |
|---|---|
| Component (B) of Example 7 | 21.9 g = 23.9 wt.-% |
| Polydimethylsiloxane, trimethylsiloxy terminated ($\eta$ = 10 mPa * s) | 1.1 g = 1.2 wt.-% |
| Pyrogenic silica Aerosil R 202 | 0.5 g = 0.5 wt.-% |
| Cristobalit-Filler (BET = 3 m$^2$/g) | 68.0 g = 77.4 wt.-% |

Catalyst Paste 4

| Component | amount = weight-% |
|---|---|
| Component (A) of Example 5 | 21.3 g = 23.3 wt.-% |
| Polydimethylsiloxane, trimethylsiloxy terminated ($\eta$ = 10 mPa * s) | 1.1 g = 1.2 wt.-% |
| Pyrogenic silica Aerosil R 202 | 0.5 g = 0.5 wt.-% |
| Cristobalit-Filler (BET = 3 m$^2$/g) | 68.0 g = 74.5 wt.-% |
| Catalyst (C) | 0.4 g = 0.5 wt.-% |

Platinum-Tetramethyl-Divinyldisiloxane-Complex in Silicone Oil (1.3 Weight-% Platinum Metal)

Base paste 4 and catalyst paste 4 were mixed at a volume ratio of base:catalyst=1:1. After 2.5 minutes setting reaction started and was finished after 9 minutes. The result was a hard product having the following characteristics.

| Compressive Strength | 114 MPa |
|---|---|
| Flexural Strength | 64 MPa |
| E-Modulus | 3562 MPa |
| Tensile Strength | 30 MPa |
| Shore hardness D | 84 |

All cured compositions of the inventive examples showed a high Shore hardness D and usually a high E-modulus. The components of the composition could be mixed easily. The cured composition did not show a smear layer.

The invention claimed is:

1. A curable dental composition comprising:
   an addition curable silicone component (A) represented by formula (3):

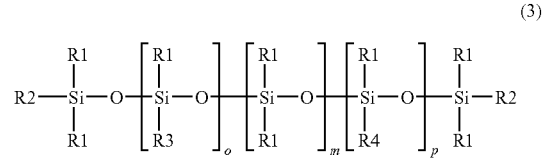

(3)

wherein:
R1=alkyl, aryl or alkaryl each comprising 1 to 20 carbon atoms, wherein at least one of the carbon atoms can be substituted with a halogen atom or alkyl group;
R2=equal to R1;
R3=alkyl, aryl or alkaryl group comprising 1 to 20 carbon atoms, wherein one or more of the H atoms can be substituted by a halogen atom;
R4=linear or branched, terminally unsaturated aliphatic, cycloaliphatic or aromatic organic or silicon organic residue moiety having (a-1) ethylenic unsaturations, and wherein such unsaturations are carbon-carbon double bonds not activated by a conjugated carbonyl group, wherein the moiety comprises 1 to 50 carbon atoms and additionally up to 6 oxygen atoms which can also be part of a ring system;
a=4, 5, 6, 7, 8, 9 or 10;
o=0 to 12;
m=0 to 50; and
p=1 to 500;
a crosslinker component (B) comprising at least 2 SiH groups;
a catalyst component (C); and
a filler component (D),
wherein the total number of carbon-carbon double bonds in component (A) is at least 3, and R4 does not comprise a vinyl group that is directly attached to a silicon atom; and
further wherein the composition, after curing, has a shore hardness D above about 35 and up to about 95, and is used as a dental material.

2. The composition according to claim 1, wherein component (A) has a viscosity less than or equal to 50 Pa*s.

3. The composition according to claim 1, wherein component (A) has a molecular weight less than or equal to 100,000 gmole$^{-1}$.

4. The composition according to claim 1, wherein the composition, after curing, has an E-modulus above 1000 Mpa.

5. The composition according to claim 1, wherein the composition, after curing, has an impact strength greater than 1 kJ/m$^2$.

6. The composition according to claim 1, wherein the composition, after curing, has a flexural strength greater than 60 Mpa.

7. The composition according to claim 1, wherein the composition, after curing, has a compressive strength greater than 100 MPa.

8. The composition according to claim 1, wherein crosslinker component (B) has a viscosity greater than 50 mPa*s.

9. The composition according to claim 1 further comprising an inhibitor component (E).

10. The composition according to claim 1 further comprising at least one component (F) selected from the group consisting of dyes, pigments, thixotropic agents, flow improvers, polymeric thickeners, surfactants, odorous substances, diluting agents and flavourings.

11. The composition according to claim 1, wherein:
component (A) is present in an amount of at least 1 wt.-%;
crosslinker component (B) is present in an amount of at least 1 wt.-%;
catalyst component (C) is present in an amount of at least 0.00005 wt.-%; and
filler component (D) is present in an amount of at least 4 wt.-% with respect to the total composition weight.

12. The composition according to claim 1, wherein component (A) is obtained via a reaction comprising the steps of reacting a compound according to formula (1)

  (1)

wherein:
A=linear or branched, terminally unsaturated, aliphatic residue, wherein the unsaturation is a C—C double bond not activated by a conjugated carbonyl group;
B=O, (O=)C—O, O—C(=O), O—C(=O)—O, NH, S;
C$^{11}$=aliphatic, cycloaliphatic, aromatic organic or silicon organic residue comprising 1 to 50, carbon atoms, and additionally, up to 6 hetero atoms which can also be part of a ring system;
a=4, 5, 6, 7, 8, 9 or 10; and
b=0 or 1
with a compound according to formula (2)

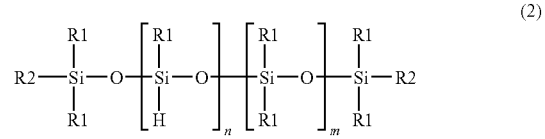  (2)

wherein
R1=alkyl, aryl or alkaryl each comprising 1 to 20 carbon atoms, wherein one or more H atoms can be substituted by halogen atoms or alkyl groups;
R2=H, R1 or alkenyl with 1 to 10 carbon atoms;
n=1 to 500, and
m=0 to 500.

13. The composition according to claim 12, wherein n is 1 to 100 and m is 0 to 100.

14. A curable dental composition comprising:
an addition curable silicone component (A) represented by formula (3):

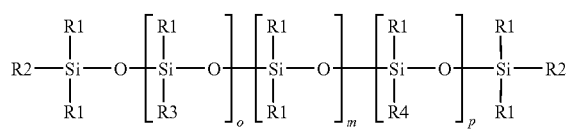  (3)

wherein:
R1=alkyl, aryl or alkaryl each comprising 1 to 20 carbon atoms, wherein at least one of the carbon atoms can be substituted with a halogen atom or alkyl group;
R2=equal to R1;
R3=alkyl, aryl or alkaryl group comprising 1 to 20 carbon atoms, wherein one or more of the H atoms can be substituted by a halogen atom;
R4=linear or branched, terminally unsaturated aliphatic, cycloaliphatic or aromatic organic or silicon organic residue moiety having (a−1) ethylenic unsaturations, and wherein such unsaturations are carbon-carbon double bonds not activated by a conjugated carbonyl group, wherein the moiety comprises 1 to 50 carbon atoms and additionally up to 6 oxygen atoms which can also be part of a ring system;
a=4, 5, 6, 7, 8, 9 or 10;
o=0 to 12;
m=0 to 50; and
p=1 to 500;
a crosslinker component (B) comprising at least 2 SiH groups;
a catalyst component (C); and
a filler component (D),
wherein the total number of carbon-carbon double bonds in component (A) is at least 3, and R4 does not comprise a vinyl group that is directly attached to a silicon atom;
wherein the composition contains filler in an amount of about 4 to about 90 wt.-%; and
further wherein the composition, after curing, has a shore hardness D above about 35 and up to about 95, and is used as a dental material.

15. The composition according to claim 14 comprising filler in an amount of about 20 to about 90 wt.-%.

16. The composition according to claim 15 comprising filler in an amount of about 20 to about 80 wt.-%.

17. The composition according to claim 1, wherein p is 1 to 100.

18. The composition according to claim 14, wherein p is 1 to 100.

19. The composition according to claim 12, wherein the compound according to formula (1) is selected from the group consisting of diallylether; diallylcarbonate; ethyleneglycoldiallylcarbonate; diethyleneglycoldiallylcarbonate; pentaerythritol-tetraallylether; di-pentaerythritol-hexaallylether; trimethylolethane-triallylether; trimethylolpropane-triallylether; ethyleneglycol-diallylether; diethyleneglycoldiallylether; 1,2-propanedioldiallylether; 1,3-propanedioldiallylether; 1,3-butanedioldiallylether; 1,4-butanedioldiallylether; 1,4-butenedioldiallylether; 1,4-butynedioldiallylether; 1,5-pentanedioldiallylether; 1,6-hexanedioldiallylether; 1,8-octanedioldiallylether; 1,9-nonanedioldiallylether; 1,10-decandioldiallylether; 1,12-dodecanedioldiallylether; glycerol-triallylether; 1,2,4-butanetrioltriallylether; 1,2,6-hexanetrioltriallylether; diglyceriol-tetraallylether; erythritol-tetraallylether; mannite-hexaallylether; sorbitol-hexaallylether; inositol-hexaallylether; oxalic acid diallylester; malonic acid diallylester; succinic acid diallylester; adipic acid diallylether; sebacic acid diallylether; dimethyldiallylsilane; divinyldimethylsilane; diphenyldiallylsilane; diphenyldivinylsilane; triallylmethylsilane; trivinylmethylsilane; tetraallylsilane; tetravinylsilane; bis-(4-allyloxyphenyl)-sulfone; bis-(4-allyloxyphenyl)-ketone; bis-(4-allyloxyphenyl)-methane; 1,1-bis-(4-allyloxyphenyl)-ethane; 2,2-bis-(4-allyloxyphenyl)-propane; 2,2-bis-(4-allyloxyphenyl)-perfluoropropane; 2,2-bis-(4-allyloxy-3,5-dibromo-phenyl)-propane; 3,3-bis-(4-allyloxyphenyl)-pentane; 4,4-bis-(4-allyloxyphenyl)-heptane; 1,1-bis-(4-allyloxyphenyl)-cyclopentane; 1,1-bis-(4-allyloxyphenyl)-cyclohexane; 1,1-bis-(4-allyloxyphenyl)-3,3,5-trimethylcyclohexane; 1,1,1-tris-(4-allyloxyphenyl)-ethane; bis-(allyloxy)-tricyclo[$5.2.1.0^{2.6}$] decane; and compounds wherein A=allyl, b=1, B=O, and C=an oligomeric backbone of 2-(methylene)ethyloxy units.

20. The composition according to claim 12, wherein the compound according to formula (2) is selected from the group consisting of methylhydrogensiloxane polymers with trimethylsiloxy endgroups; methylhydrogensiloxane polymers with dimethylhydrogensiloxy endgroups; methylhydrogensiloxane-co-dimethylsiloxane copolymers with trimethylsiloxy endgroups; methylhydrogensiloxane-co-dimethylsiloxane copolymers with dimethylhydrogensiloxy endgroups; phenylhydrogensiloxane polymers with trimethylsiloxy endgroups; phenylhydrogensiloxane polymers with dimethylhydrogensiloxy endgroups; phenylhydrogensiloxane-co-dimethylsiloxane copolymers with trimethylsiloxy endgroups; phenylhydrogensiloxane-co-dimethylsiloxane copolymers with dimethylhydrogensiloxy endgroups; methylhydrogensiloxane-co-phenylmethylsiloxane copolymers with trimethylsiloxy endgroups; methylhydrogensiloxane-co-phenylmethylsiloxane copolymers with dimethylhydrogensiloxy endgroups; dimethylsiloxane polymers with dimethylhydrogensiloxy endgroups; diphenylsiloxane-polymers with dimethylhydrogensiloxy endgroups; and phenylmethylsiloxane polymers with dimethylhydrogensiloxy endgroups.

* * * * *

UNITED STATES PATENT AND TRADEMARK OFFICE
CERTIFICATE OF CORRECTION

| | |
|---|---|
| PATENT NO. | : 7,807,730 B2 |
| APPLICATION NO. | : 11/247040 |
| DATED | : October 5, 2010 |
| INVENTOR(S) | : Peter Bissinger et al. |

It is certified that error appears in the above-identified patent and that said Letters Patent is hereby corrected as shown below:

Column 3
Line 28, delete "disolved" and insert -- dissolved --, therefor.

Column 6
Line 8, delete "decan" and insert -- decane --, therefor.
Line 19, delete "Karsted" and insert -- Karstedt --, therefor.

Column 11-12
Line 1-37, delete

"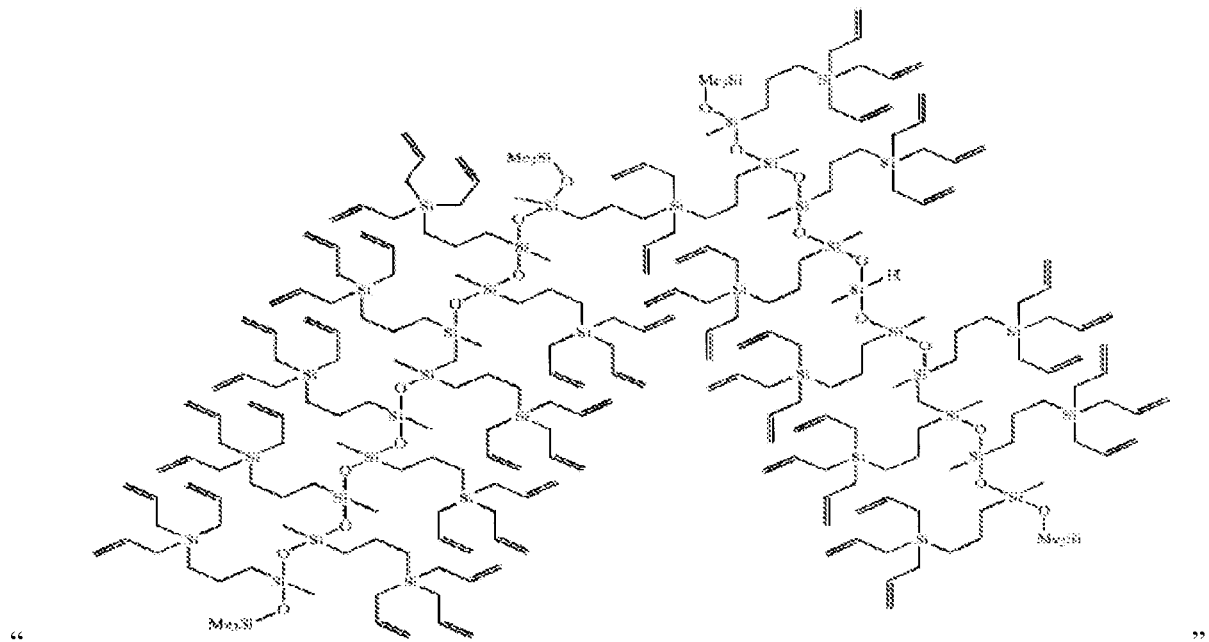"

Signed and Sealed this
Twenty-ninth Day of March, 2011

David J. Kappos
*Director of the United States Patent and Trademark Office* and insert

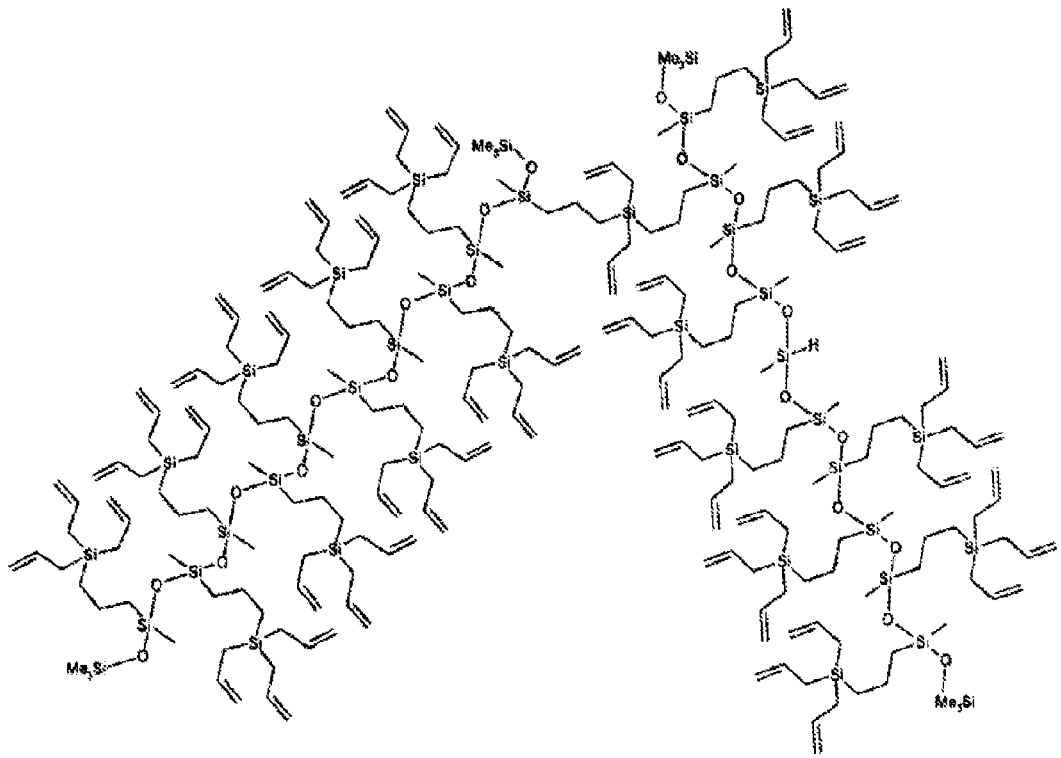

--
therefor.

Column 13
Line 43, delete "Diglyceriol" and insert -- Diglycerol --, therefor.

Column 14
Line 17, delete "keton" and insert -- ketone --, therefor.
Line 60-61, delete "Engeneering" and insert -- Engineering --, therefor.

Column 17
Line 8, delete "Typ" and insert -- Type --, therefor.
Line 17, delete "NV). the" and insert -- NV). The --, therefor.

Column 18
Line 63, delete "tolulene" and insert -- toluene --, therefor.

Column 20
Line 31, delete "Cupfferone" and insert -- Cupferron --, therefor.
Line 40, delete "Poly(Hydrogene" and insert -- Poly(Hydrogen --, therefor.
Line 41, delete "Bisphenole" and insert -- Bisphenol --, therefor.
Line 62, delete "Poly(hydrogene" and insert -- Poly(hydrogen --, therefor.
Line 64, delete "Cupferrone" and insert -- Cupferron --, therefor.
Line 65, delete "Bisphenole" and insert -- Bisphenol --, therefor.
Line 67, delete "spectum" and insert -- spectrum --, therefor.

CERTIFICATE OF CORRECTION (continued)
U.S. Pat. No. 7,807,730 B2

Column 21
Line 6, delete "Poly(Hydrogene" and insert -- Poly(Hydrogen --, therefor.
Line 27, delete "Poly(hydrogene" and insert -- Poly(hydrogen --, therefor.
Line 28-29, delete "Methoxyphenole" and insert -- Methoxyphenol --, therefor.
Line 32, delete "spectum" and insert -- spectrum --, therefor.

Column 27
Line 25, in Claim 19, delete "diglyceriol" and insert -- diglycerol --, therefor.